: US005910403A

United States Patent [19]
Hellerstein

[11] Patent Number: 5,910,403
[45] Date of Patent: Jun. 8, 1999

[54] METHODS FOR MEASURING CELLULAR PROLIFERATION AND DESTRUCTION RATES IN VITRO AND IN VIVO

[75] Inventor: Marc K. Hellerstein, Kensington, Calif.

[73] Assignee: The Regents of University of California, Oakland, Calif.

[21] Appl. No.: 08/857,007

[22] Filed: May 15, 1997

[51] Int. Cl.⁶ .................................................... C12Q 1/00
[52] U.S. Cl. ..................................... 435/4; 435/6; 435/29
[58] Field of Search ........................... 435/4, 6, 29, 91.2, 435/91.1; 935/77

[56] References Cited

U.S. PATENT DOCUMENTS 5,338,686  8/1994  Hellerstein .............................. 436/173
5,439,803  8/1995  Ross et al. ................................ 435/14

FOREIGN PATENT DOCUMENTS

WO90/11371  10/1990  WIPO.
WO93/25705  12/1993  WIPO.

OTHER PUBLICATIONS

Park, S. S., et al., "Measurement of small intestinal cell turnover with [6,6, 2H2] glucose," *Berkeley Scientific* vol. 1, No. 2 (1997), pp. 41–43.
Wolfe, R. R., "Isotopic Measurement of Glucose and Lactate Kinetics," *Ann. Med.,* vol. 22 (1990), pp. 163–170.
Smith, et al., "The Phosphogluconate Odixative Pathway," Principles of Biochemistry, 7ᵗʰ edition, *McGraw–Hill Book Company,* (1983), pp. 417–423.
McCallan, et al., "Measurement of cell proliferation by labeling of DNA with stable isotope–labeled glucose: Studies in vitro, in animals, and in humans," *Proc. Natl. Acad. Sci. USA,* vol. 95 Jan. 1998, pp. 708–713.
Adami, H.O. et al., "The aetiology and pathogenesis of human breast cancer," *Mutation Research* 333:29–35 (1995).
Asher, E. et al., "Evaluation of Cell Death in EBV–Transformed Lymphocytes Using Agarose Gel Electrophoresis, Light microscopy and Electron Microscopy," *Leukemia and Lymphoma* 19:107–119 (1995).
Cohen, A. et al., "Purine and Pyrimidine Metabolism in Human T Lymhocytes," *J. Biol. Chem.* 258(20):12334–12340 (1983).
Crain, P.F., "Preparation and Enzymatic Hydrolysis of DNA and RNA for Mass Spectrometry," *Meth. Enz.* 193:782–790 (1990).
Gratzner, H.G., "Monoclonal Antibody to 5–Broma–and 5–Iododeoxyuridine: A New Reagent for Detection of DNA Replication," *Science* 218:474–475 (1982).
Hellerstein, M.A. et al., "Glycoconjugates as noninvasive probes of intrahepatic metabolism: Pathways of glucose entry into compartmentalized hepatic UDP–glucose pools during glycogen accumulation," *Proc. Natl. Acad. Sci. U.S.A.* 83:7044–7048 (1986).
Hellerstein, M.A. et al., "Mass isotopomer distribution analysis: a technique for measuring biosynthesis and turnover of polymers," *Am. J. Physiol.* 263:E988–E1001 (1992).
Ho, D.D. et al., "Rapid turnover of plasma virions and CD4 lymphocytes in HIV–1 infection," *Nature* 373:123–126 (1995).
Lipkin, M., "Proliferation and Differentiation of Normal and Diseased Gastrointestinal Cells," *Physiol. Gastro. Tract,* Johnson, L.R. ed., Raven Press, New York, pp. 255–284 (1987).
McCloskey, J.A., "ElectronIonization Mass Spectra of Trimethylsilyl Derivatives of Nucleosides," *Meth. Enz.* 193:825–841 (1990).
Neese, R.A. et al., "Gluconeogenesis and Intrahepatice Triose Phosphate Flux in Response to Fasting or Substrate Loads," *J. Biol. Chem.* 270 (24) :14452–14463.
Patterson, B.W. et al., "Concentration Dependence of Methyl Palmitate Isotope Ratios by Electron Impact Ionization Gas Chromatography/Mass Spectrometry," *Biol. Mass Spect.* 22:481–486 (1993).
Reichard, P., "From deoxynucleotides to DNA synthesis," *Fed. Proc.* 37 (1) :9–14 (1978).
Reichard, P., "Interactions Between Deoxyribonucleotide and DNA Synthesis," *Ann. Rev. Biochem.* 57:349–374 (1988).
Rocha, B. et al., "Accumulation of bromodeoxyuridine–labeled cells in central and peripheral lymphoid organs: minimal estimates of production and turnover rates of mature lymphocytes," *Eur. J. Immunol.* 20:1697–1708 (1990).
Sawada, S. et al., "Comparison of autoradiography, liquid scintillation counting and immunoenzymatic staining of 5–bromo–2'–deoxyuridine for measurement of unscheduled DNA synthesis and replicative DNA synthesis in rat liver," *Mutation Research,* 344:109–116 (1995).
Shigenaga, M.K. et al., Assays of Oxidative DNA Damage Biomarkers 8–Oxo–2'deoxyguanosine and 8–Oxoguanine in Nuclear DNA and Biological Fluids by High–Performance Liquid Chromatography with Electrochemical Detection, *Meth. Enz.* 234:16–33 (1994).
Sprent, J. et al., "CD4⁺ cell turnover," *Nature* 375:194 (1995).

(List continued on next page.)

*Primary Examiner*—Ralph Gitomer
*Attorney, Agent, or Firm*—Townsend & Townsend & Crew LLP

[57] ABSTRACT

The present invention relates to methods for measuring the proliferation and destruction rates of cells by measuring deoxyribonucleic acid (DNA) synthesis. In particular, the methods utilize non-radioactive stable isotope labels to endogenously label DNA synthesized through the de novo nucleotide synthesis pathway in a cell. The amount of label incorporated in the DNA is measured as an indication of cellular proliferation. Such methods do not involve radioactivity or potentially toxic metabolites, and are suitable for use both in vitro and in vivo. Therefore, the invention is useful for measuring cellular proliferation in humans for the diagnosis of a variety of disease conditions in which cellular proliferation is involved.

16 Claims, 8 Drawing Sheets

OTHER PUBLICATIONS

Traber, P.G. et al., "Isolation of intestinal epithelial cells for the study of differential gene expression along the crypt–villus axis," *Am. J. Physiol.* 260:G895–G903 (1991).

Waldeman, F.M. et al., "A Comparison between Bromodeoxyuridine and $^3$H Thymidine Labeling in Human Breast Tumors," *Modern Path.* 4(6):718–722 (1991).

Wei, X et al., "Viral dynamics in human immunodeficiency virus type 1 infection," *Nature* 373:117–122 (1995).

Wolthers, K.C. et al., "T Cell Telomere Length in HIV–1 Infection: No Evidence for Increased CD4$^+$ T Cell Turnover," *Science* 274:1543–1547 (1996).

Wood, H.G. et al., "Estimation of Pathways of Carbohydrate Metabolism," *Biochem. Zeitschrift,* 338:809–847 (1963).

*Handbood of Derivatives for Chromatography,* Blau and Halket, eds., John Wiley & Sons, UK, (1993) Table of Contents.

Park S., Measurement of Small Intestinal Cell Turnover with [6,6,2H2]Glucose, Berkeley Scientific 1(2)41–43, Mar. 1997.

MacAllan D., Measurement of Cell Proliferation by Labeling of DNA with Stable Isotope Labeled Glucose: Studies in vitro, in Animals, and in Humans, Proc Natl Acad Sci USA, 95:708–713, Jan. 1998.

FIG. 8

METHODS FOR MEASURING CELLULAR PROLIFERATION AND DESTRUCTION RATES IN VITRO AND IN VIVO

1. INTRODUCTION

The present invention relates to methods for measuring the proliferation and destruction rates of cells by measuring deoxyribonucleic acid (DNA) synthesis. In particular, the methods utilize non-radioactive stable isotope labels to endogenously label DNA synthesized through the de novo nucleotide synthesis pathway in a cell. The amount of label incorporated in the DNA is measured as an indication of cellular proliferation. Such methods do not involve radioactivity or potentially toxic metabolites, and are suitable for use both in vitro and in vivo. Therefore, the invention is useful for measuring cellular proliferation in humans for the diagnosis of a variety of disease conditions in which cellular proliferation is involved.

2. BACKGROUND OF THE INVENTION

Control of cell proliferation is important in all multicellular organisms. A number of pathologic processes, including cancer and acquired immunodeficiency syndrome (AIDS) (Ho et al., 1995, *Nature* 373:123–126; Wei et al., 1995, *Nature* 373:117–122; Adami et al., 1995, *Mutat. Res.* 333:29–35), are characterized by failure of the normal regulation of cell turnover. Measurement of the in vivo turnover of cells would therefore have wide applications, if a suitable method were available. Prior to the present invention, direct and indirect techniques for measuring cell proliferation or destruction existed, but both types were flawed.

Direct measurement of cell proliferation generally involves the incorporation of a labeled nucleoside into genomic DNA. Examples include the tritiated thymidine ($^3$H-dT) and bromodeoxyuridine (BrdU) methods (Waldman et al., 1991, *Modern Pathol.* 4:718–722; Gratzner, 1982, *Science* 218:474–475). These techniques are of limited applicability in humans, however, because of radiation induced DNA damage with the former (Asher et al., 1995, *Leukemia and Lymphoma* 19:107–119) and toxicities of nucleoside analogues (Rocha et al., 1990, *Eur. J. Immunol.* 20:1697–1708) with the latter.

Indirect methods have also been used in specific cases. Recent interest in CD4$^+$ T lymphocyte turnover in AIDS, for example, has been stimulated by indirect estimates of T cell proliferation based on their rate of accumulation in the circulation following initiation of effective anti-retroviral therapy (Ho et al., 1995, *Nature* 373:123–126; Wei et al., 1995, *Nature* 373:117–122). Unfortunately, such indirect techniques, which rely on changes in pool size, are not definitive. The increase in the blood T cell pool size may reflect redistribution from other pools to blood rather than true proliferation (Sprent and Tough, 1995, *Nature* 375:194; Mosier, 1995, *Nature* 375:193–194). In the absence of direct measurements of cell proliferation, it is not possible to distinguish between these and other (Wolthers et al., 1996, *Science* 274:1543–1547) alternatives.

Measurement of cell proliferation is of great diagnostic value in diseases such as cancer. The objective of anti-cancer therapies is to reduce tumor cell growth, which can be determined by whether tumor DNA is being synthesized or being broken down. Currently, the efficacy of therapy, whether chemotherapy, immunologic therapy or radiation therapy, is evaluated by indirect and imprecise methods such as apparent size by x-ray of the tumor. Efficacy of therapy and rational selection of combinations of therapies could be most directly determined on the basis of an individual tumor's biosynthetic and catabolic responsiveness to various interventions. The model used for bacterial infections in clinical medicine—culture the organism and determine its sensitivities to antibiotics, then select an antibiotic to which it is sensitive—could then be used for cancer therapy as well. However, current management practices proceed without the ability to determine directly how well the therapeutic agents are working.

A long-standing vision of oncologists is to be able to select chemotherapeutic agents the way antibiotics are chosen—on the basis of measured sensitivity to each drug by the tumor of the patient in question. The ability to measure cancer cell replication would place chemotherapy selection and research on an equal basis as antibiotic selection, with great potential for improved outcomes.

Accordingly, there remains a need for a generally applicable method for measuring cell proliferation that is without hazard and can be applied in the clinical arena.

3. SUMMARY OF THE INVENTION

The present invention relates to methods for measuring cellular proliferation and destruction rates by measuring DNA synthesis. In particular, it relates to the use of a non-radioactive stable isotope label to endogenously label DNA synthesized by the de novo nucleotide synthesis pathway in a cell. The label incorporated into the DNA during DNA synthesis is readily detectable by methods well known in the art. The amount of the incorporated label can be measured and calculated as an indication of cellular proliferation and destruction rates.

The invention is based, in part, on the Applicants' discovery that DNA synthesis can be measured by labeling the deoxyribose ring with a stable isotope label through the de novo nucleotide synthesis pathway. Cellular proliferation was measured in vitro, in an animal model and in humans. In vitro, the proliferation of two cell lines in log phase growth was measured by the methods of the invention and was shown to be in close quantitative agreement with the increased number of cells by direct cell counting, which is considered the least ambiguous measure of cell proliferation. In animals, the methods of the invention were also shown to be consistent with values estimated previously by independent techniques. For example, thymus and intestinal epithelium were shown to be rapid turnover tissues, while turnover of liver cells was much slower. In humans, the observed pattern of a lag phase followed by rapid appearance of a cohort of labeled granulocytes is also consistent with previous observation.

Figure 1:
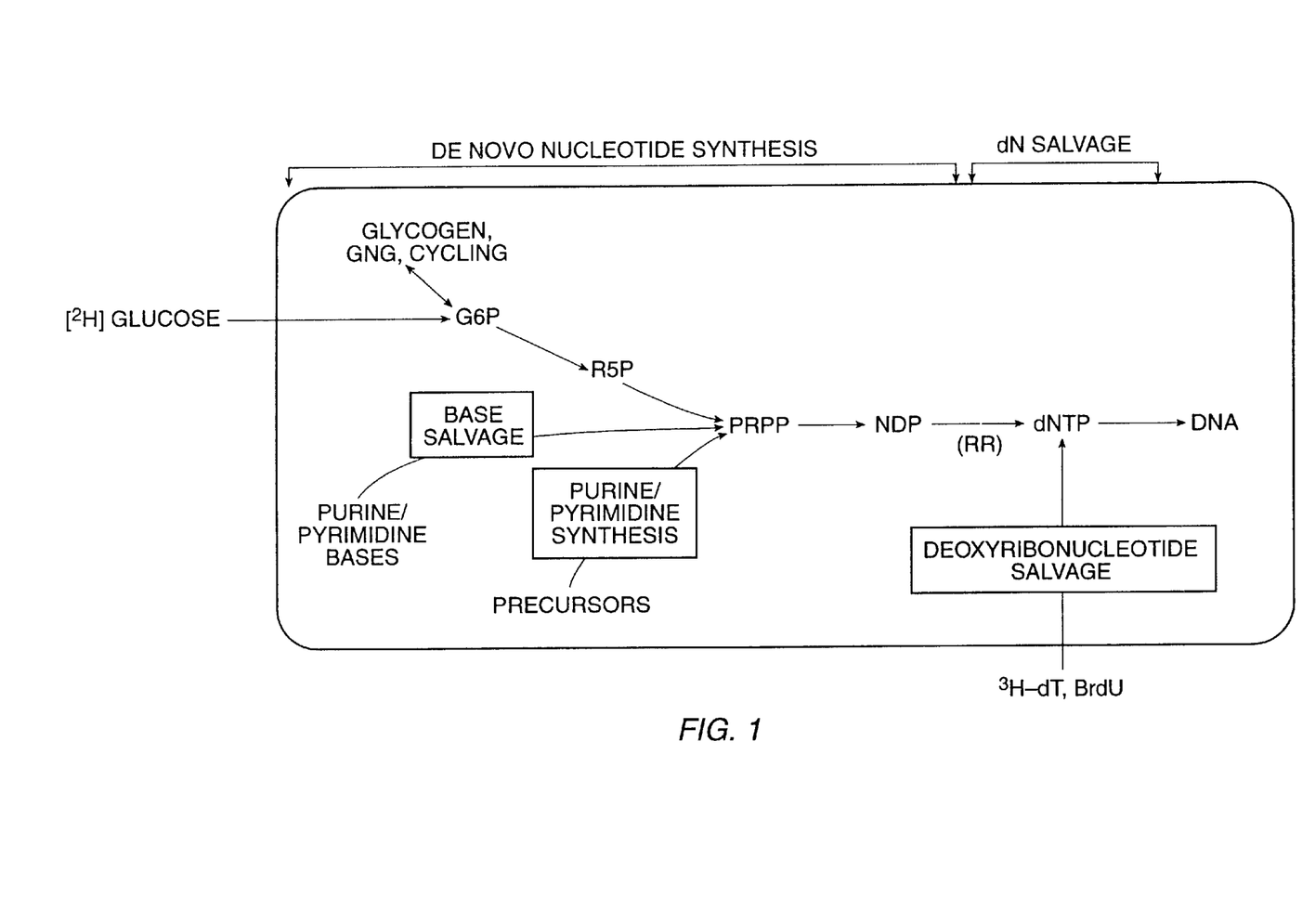

The methods differ from conventional labeling techniques in 3 major respects. First, conventional isotopic methods label DNA through the nucleoside salvage pathway, whereas the methods of the invention label deoxyribonucleotides in DNA by the de novo nucleotide synthesis pathway (FIG. 1). Labeling via this pathway is advantageous because in most cells that enter the S-phase of the cell cycle, the key enzymes controlling de novo synthesis of deoxyribonucleotide-triphosphates (dNTP's), in particular ribonucleotide reductase (RR), are upregulated, whereas the enzymes of the nucleoside salvage pathway are suppressed (Reichard, 1978, *Fed. Proc.* 37:9–14; Reichard, 1988, *Ann Rev. Biochem.* 57:349–374; Cohen et al., 1983, *J. Biol. Chem.* 258:12334–12340).

Second, the label can be detected in the methods of the invention in purine deoxyribonucleosides instead of pyrimidines (e.g. from $^3$H-dT or BrdU). This is advantageous because the de novo synthesis pathway tends to be more active for purine than pyrimidine dNTP's (Reichard, 1978, Fed. Proc. 37:9–14; Reichard, 1988, Ann Rev. Biochem. 57:349–374; Cohen et al., 1983, J. Biol. Chem. 258:12334–12340). In fact, regulatory deoxyribonucleotides have been shown in lymphocytes (Reichard, 1978, Fed. Proc. 37:9–14; Reichard, 1988, Ann Rev. Biochem. 57:349–374) to exert negative feedback on RR for pyrimidine dNTP synthesis but positive feedback for purine dNTP synthesis, ensuring that the de novo synthesis pathway is always active for the purines but is variable for the pyrimidines.

More importantly, the methods of the invention use stable isotope labels instead of radio-isotopes, and thus are safe for human use. Therefore, a wide variety of uses are encompassed by the invention, including, but not limited to, measurement of cellular proliferation and/or destruction in conditions where such information is of diagnostic value such as cancer, AIDS, hematologic disorders, endocrine disorders, bone disorders and organ failure.

4. BRIEF DESCRIPTION OF THE DRAWINGS

FIG. 1. Biochemistry of DNA synthesis and routes of label entry. Not all intermediates are shown. G6P, glucose-6-phosphate; R5P, ribose-5-phosphate; PRPP, phosphoribosepyrophosphate; DNNS, de novo nucleotide synthesis pathway; NDP, ribonucleoside-diphosphates; RR, ribonucleoside reductase; dN, deoxyribonucleoside; dNTP, deoxyribonucleoside-triphosphate; $^3$H-dT, tritiated thymidine; BrdU, bromodeoxyuridine.

FIGS. 4A–4D. Labeling of tissue culture cells during log-phase growth in vitro. Enrichment of dA from cellular DNA in hepatocyte (HepG2) (4A) and lymphocyte (H9) (4B) cell lines grown in media enriched with [6,6-$^2$H$_2$] glucose. Lymphocyte data include results from experiments at two different glucose enrichments.

FIGS. 6A–6B.

5. DETAILED DESCRIPTION OF THE INVENTION

The biochemical correlate of new cell production is DNA synthesis. DNA synthesis is also relatively specific for cell division because "unscheduled" DNA synthesis is quantitatively minor (Sawada et al., 1995, Mutat. Res. 344:109–116). Therefore, measurement of new DNA synthesis is essentially synonymous with measurement of cell proliferation.

The methods for measuring cell proliferation described herein have several advantages over previously available methods. $^3$H-Thymidine is a potent anti-metabolite that has been used to kill dividing cells (Asher et al., 1995, Leukemia and Lymphoma 19:107–119); the toxicity of introducing radio-isotopes into DNA is avoided by the methods of the invention which utilize stable isotopes. The toxicities of nucleoside analogues, e.g. BrdU, are also avoided by labeling with a physiologic substrate through endogenous synthetic pathways.

Isotopic contamination by non-S-phase DNA synthesis is also minimized by labeling through the de novo nucleotide synthesis pathway, which is primarily active during S-phase. The variability of labeled pyrimidine nucleoside salvage uptake is resolved by labeling purine dNTP's via the de novo nucleotide synthesis pathway; turning what was previously a disadvantage (low purine dNTP labeling from the nucleoside salvage pathway) into an advantage (high and constant labeling from the de novo pathway). This is demonstrated by the constancy of [6,6-$^2$H$_2$] glucose incorporation into DNA even in the presence of supraphysiologic extracellular concentrations of deoxyribonucleosides (Table 1). Possible input from free purine or pyrimidine base salvage does not dilute the ribose moiety of NTP's, because the salvage pathway for free bases, like de novo synthesis of bases, involves combination with PRPP, which is synthesized from glucose (FIG. 1).

Moreover, re-utilization of label from catabolized DNA is avoided by analyzing purine deoxyribonucleotides, because the deoxyribonucleoside salvage pathway is low for purines. Die-away curves of labeled dA or dG in DNA after cessation of labeling will therefore be relatively uncontaminated by isotope re-utilization, and cell turnover should be measurable from decay curves as well as incorporation curves (Hellerstein and Neese, 1992, Am J. Physiol. 263:E988–E1001).

Finally, the methods of the invention provide a quantitative measure for enumerating numbers of new cells as opposed to conventional methods which only detect the relative increase or decrease of cell numbers as compared to controls.

Although the specific procedures and methods described herein are exemplified using labeled glucose as the precursor and detection of the label by analyzing purine deoxyribonucleosides, they are illustrative for the practice of the invention. Analogous procedures and techniques, as well as functionally equivalent labels, as will be apparent to those of skill in the art based on the detailed disclosure provided herein, are also encompassed by the invention.

5.1. Stable Isotope Labels for use in Labeling DNA during De Novo Biosynthesis of Nucleotides The present invention relates to methods of measuring cellular proliferation by contacting a cell with a stable isotope label for its incorporation into DNA via the de novo nucleotide synthesis pathway. Detection of the incorporated label is used as a measure of DNA synthesis. Labeling DNA through the de novo nucleotide synthesis (endogenous) pathway has several advantages over conventional labeling methods through the nucleoside salvage (exogenous) pathway. These include non-toxicity, specificity for S-phase of the cell cycle and absence of re-incorporation of the label from catabolized DNA. The use of a non-radioactive label further reduces the risks of mutation.

In a specific embodiment illustrated by way of example in Section 6, infra, $[6,6-^2H_2]$ glucose, $[U-^{13}C_6]$ glucose and $[2-^{13}C_1]$ glycerol were used to label the deoxyribose ring of DNA. Labeling of the deoxyribose is superior to labeling of the information-carrying nitrogen bases in DNA because it avoids variable dilution sources. The stable isotope labels are readily detectable by mass spectrometric techniques.

In a preferred embodiment of the invention, a stable isotope label is used to label the deoxyribose ring of DNA from glucose, precursors of glucose-6-phosphate or precursors of ribose-5-phosphate. In embodiments where glucose is used as the starting material, suitable labels include, but are not limited to, deuterium-labeled glucose such as $[6,6-^2H_2]$ glucose, $[1-^2H_1]$ glucose, $[3-^2H_1]$ glucose, $[^2H_7]$ glucose, and the like; $^{13}C$-1 labeled glucose such as $[1-^{13}C_1]$ glucose, $[U-^{13}C_6]$ glucose and the like; and $^{18}O$-labeled glucose such as $[1-^{18}O_2]$ glucose and the like.

In embodiments where a glucose-6-phosphate precursor or a ribose-5-phosphate precursor is desired, a gluconeogenic precursor or a metabolite capable of being converted to glucose-6-phosphate or ribose-5-phosphate may be used. Gluconeogenic precursors include, but are not limited to, $^{13}C$-labeled glycerol such as $[2-^{13}C_1]$ glycerol and the like, a $^{13}C$-labeled amino acid, deuterated water ($^2H_2O$) and $^{13}C$-labeled lactate, alanine, pyruvate, propionate or other non-amino acid precursors for gluconeogenesis. Metabolites which are converted to glucose-6-phosphate or ribose-5-phosphate include, but are not limited to, labeled ($^2H$ or $^{13}C$) hexoses such as $[1-^2H_1]$ galactose, $[U-^{13}C]$ fructose and the like; labeled ($^2H$ or $^{13}C$) pentoses such as $[1-^{13}C_1]$ ribose, $[1-^2H_1]$ xylitol and the like, labeled ($^2H$ or $^{13}C$) pentose phosphate pathway metabolites such as $[1-^2H_1]$ seduheptalose and the like, and labeled ($^2H$ or $^{13}C$) amino sugars such as $[U-^{13}C]$ glucosamine, $[1-^2H_1]$ N-acetyl-glucosamine and the like.

The present invention also encompasses stable isotope labels which label purine and pyrimidine bases of DNA through the de novo nucleotide synthesis pathway. Various building blocks for endogenous purine synthesis may be used to label purines and they include, but are not limited to, $^{15}N$-labeled amino acids such as $[^{15}N]$ glycine, $[^{15}N]$ glutamine, $[^{15}N]$ aspartate and the like, $^{13}C$-labeled precursors such as $[1-^{13}C_1]$ glycone, $[3-^{13}C_1]$ lactate, $[^{13}C]HCO_3$, $[^{13}C]$ methionine and the like, and $^2H$-labeled precursors such as $^2H_2O$. Various building blocks for endogenous pyrimidine synthesis may be used to label pyrimidines and they include, but are not limited to, $^{15}N$-labeled amino acids such as $[^{15}N]$ glutamine and the like, $^{13}C$-labeled precursors such as $[^{13}C]HCO_3$, $[U-^{13}C_4]$ aspartate and the like, and $^2H$-labeled precursors ($^2H_2O$).

It is understood by those skilled in the art that in addition to the list above, other stable isotope labels which are substrates or precursors for any pathways which result in endogenous labeling of DNA are also encompassed within the scope of the invention. The labels suitable for use in the present invention are generally commercially available or can be synthesized by methods well known in the art.

5.2. Detection of Incorporated Label in DNA

The level of incorporation of stable isotope label into the DNA of cells is determined by isolating the DNA from a cell population of interest and analyzing for isotope content a chemical portion of the DNA molecule that is able to incorporate label from an endogenous labeling pathway using standard analytical techniques, such as, for example, mass spectroscopy, nuclear magnetic resonance, and the like. Methods of sample preparation will depend on the particular analytical techniques used to detect the presence of the isotopic label, and will be apparent to those of skill in the art.

In a preferred embodiment of the invention, the presence of the label is detected by mass spectrometry. For this method of detection, tissue or cells of interest are collected (e.g., via tissue biopsy, blood draw, collection of secretia or excretion from the body, etc.) and the DNA extracted using standard techniques as are well-known in the art. Of course, the actual method of DNA isolation will depend on the particular cell type, and will be readily apparent to those of skill in the art. The cells may be optionally further purified prior to extracting the DNA using standard techniques, such as, for example, immuno-affinity chromatography, fluorescence-activated cell sorting, elutration, magnetic bead separation, density gradient centrifugation, etc.

The DNA is then hydrolyzed to deoxyribonucleosides using standard methods of hydrolysis as are well-known in the art. For example, the DNA can be hydrolyzed enzymatically, such as for example with nucleases or phosphatases, or non-enzymatically with acids, bases or other methods of chemical hydrolysis.

Deoxyribonucleosides are then prepared for mass spectrometric analysis using standard techniques (e.g., synthesis of trimethylsilyl, methyl, acetyl, etc. derivatives; direct injection for liquid chromatography; direct probe sample introduction, etc.) and the level of incorporation of label into the deoxyribonucleosides determined.

The mass spectrometric analysis is of fragment potentially containing stable isotope label introduced from endogenous labeling pathway. For example, the m/z 467–469 fragment of the deoxyadenosine or the m/z 557 and 559 fragment of the deoxyguanosine mass spectrum, which contain the intact deoxyribose ring, could be analyzed after $[6,6-^2H_2]$ glucose administration, using a gas chromatograph/mass spectrometer under electron impact ionization and selected ion recording mode. Or the m/z 103 and 104 fragment of the deoxyadenosine mass spectrum, which contains the position C-5 of deoxyribose, could be analyzed after administration of $[6,6-^2H]$ glucose or $[6-^{13}C_1]$ glucose. In a preferred embodiment, the mass spectrometric fragment analyzed is from purine deoxyribonucleosides rather than pyrimidine deoxyribonucleosides.

The fraction of newly synthesized DNA and therefore newly divided cells (cell proliferation or input rate) or newly removed cells (cell death or exit rate) is then calculated (Table 1).

TABLE 1

| Day # | abundances m/z 457 | abundances m/z 459 | dA* enrichment | f (uncorrected) (% new cells) | f (corrected) (% new cells) |
|---|---|---|---|---|---|
| 1 (Baseline) | 2844049 | 518152 | 0.00000 | 0.00 | 0.00 |
| 2 | 1504711 | 260907 | 0.00000 | 0.00 | 0.00 |
| 3 | 2479618 | 453609 | 0.00298 | 2.50 | 3.84 |
| 4 | 3292974 | 624718 | 0.00586 | 4.91 | 7.55 |
| 5 | 2503144 | 461905 | 0.00451 | 3.77 | 5.81 |
| 6 | 1055618 | 186087 | 0.00318 | 2.66 | 4.09 |
| 7 | 2186009 | 394058 | 0.00193 | 1.61 | 2.48 |
| 8 | 2154805 | 389390 | 0.00250 | 2.09 | 3.22 |
| 9 | 2472480 | 455139 | 0.00417 | 3.49 | 5.38 |
| 10 | 1532187 | 272195 | 0.00238 | 2.00 | 3.07 |

Abundances represent average of three acquisitions.
Plasma glucose enrichment = 11.9%; dA* = deoxyadenosine enrichment based on comparison to abundance corrected standard curve of $[5,5-^2H_2]$deoxyadenosine; f uncorrected, calculated as dA enrichment divided by plasma glucose enrichment; f corrected, calculated as dA enrichment divided by 0.65 times plasma glucose enrichment

5.3. Uses

5.3.1. In Vitro Uses

In a specific embodiment illustrated by way of example in Section 6, infra, an enrichment of deoxyadenosine (dA) observed in two cell types incubated with a stable isotope label and grown as monolayers and in suspension. The dA enrichment correlated closely with the increase in cell numbers by direct counting. Therefore, the methods of the invention may be used to measure cellular proliferation in a variety of proliferative assays. For instance, bioassays which use cellular proliferation as a read-out in response to a growth factor, hormone, cytokine or inhibitory factor may be developed by using a stable isotope label which targets the de novo nucleotide synthesis pathway. Examples of such assays include lymphocyte activation by antigen and antigen-presenting cells, apoptosis of target cells induced by tumor necrosis factor and cytotoxicity of tumor cells by cytolytic lymphocytes.

5.3.2. In Vivo Uses

Since the methods of the invention do not involve radioactivity and potentially toxic metabolites, these methods are particularly useful as a diagnostic tool in measuring cellular proliferation and destruction rates in vivo. In comparison to conventional methods in humans, the methods of the invention are safe, more widely applicable, more easily performed, more sensitive and produce more accurate results because the de novo nucleotide synthesis pathway is constant and predominant, is not diluted, label via physiologic substrates rather than potentially toxic, non-physiologic metabolites, do not require preservation of cell or tissue anatomy and involve no radioactivity.

A wide variety of medical applications in which cellular proliferation and destruction play an important role are encompassed by the present invention. In particular the methods of the invention may be used to determine the proliferation and destruction rates in cancer, infectious diseases, immune and hematologic conditions, organ failure and disorders of bone, muscle and endocrine organs.

5.3.2.1. Cancer Treatments

In one embodiment of the invention, a patient could receive systemic or local administration of a stable isotope labeled precursor for the de novo nucleotide synthesis pathway (e.g., $[6,6-^2H_2]$ glucose at 1.25 g/hr for 24–48 hr intravenously) prior to initiation of chemotherapy, and again 1–2 weeks after starting chemotherapy. A small specimen of the turnover (e.g., by skinny needle aspiration) is performed after each period of stable isotope administration in the synthesis rate of DNA, reflecting inhibition of tumor cell division, could be used as a treatment end-point for selecting the optimal therapy. Typically, the dose of isotope precursor given is enough to allow incorporation into deoxyribonucleosides above the mass spectrometric detection limits. Samples are taken depending on tracer dilution and cell turnover rates.

5.3.2.2. Cancer Prevention

The risk for breast, colon and other cancers tends to vary with proliferative stress in the tissue, i.e., hormones, inflammation or dietary factors that alter cell proliferation profoundly affect cancer rates. The ability to characterize a woman's underlying mammary cell proliferative stress and its response to preventative intervention in early adult life, for example, would radically alter breast cancer prevention. The same applies to colon cancer, lung cancer, and other cancers.

5.3.2.3. Aids

Anti-retrovirals in AIDS are intended to block viral replication (a biosynthetic process) in order to reduce $CD4^+$ T cell death and turnover. Recent advances in AIDS treatment have focused precisely on these kinetic processes, although direct kinetic measurements were not available. The ability to measure directly these treatment end-points can radically change the nature of HIV therapeutics. Physicians can quickly determine whether to begin aggressive anti-retroviral treatment early in the disease for each individual patient. In a specific embodiment illustrated by way of example in Section 6, infra, the methods of the invention are used to accurately measure the proliferation and destruction rates of $CD4^+$ cells in HIV patients.

5.3.2.4. Conditions in Which Cellular Proliferation is Involved

A large number of conditions are known to be characterized by altered cellular proliferation rates and thus can be monitored by methods of the invention:

Cancer: Malignant tumors of any type (e.g., breast, lung, colon, skin, lymphoma, leukemia, etc.); pre-cancerous conditions (e.g., adenomas, polyps, prostatic hypertrophy, ulcerative colitis, etc.); factors modulating risk for common cancers (e.g., estrogens and breast epithelial cells; dietary fat and colonocytes; cigarette smoking or anti-oxidants and bronchial epithelial cells; hormones and prostate cells, etc.).

Immune disorders: $CD4^+$ and $CD8^+$ T lymphocytes in AIDS; T and B lymphocytes in vaccine-unresponsiveness; T cells in autoimmune disorders; B cells in hypogammaglobulinemias; primary immunodeficiencies (thymocytes); stress-related immune deficiencies (lymphocytes); and the like.

Hematologic conditions: White blood cell deficiencies (e.g., granulocytopenia); anemias of any type; myeloproliferative disorders (e.g., polycythemia vera); tissue white cell infiltrative disorders (e.g., pulmonary interstitial eosinophilia, lymphocytic thyroiditis, etc.); lymphoproliferative disorders; monoclonal gammopathies; and the like.

Organ failure: Alcoholic and viral hepatitis (liver cells); diabetic nephropathy (glomerular or mesangeal cells); myotrophic conditions (myocytes); premature gonadal failure (oocytes, stromal cells of ovary, spermatocytes, Leydig cells, etc.); and the like.

Conditions of bone and muscle: Response to exercise training or physical therapy (myocytes or mitochondria in myocytes); osteoporosis (osteoclast, osteoblasts, parathyroid cells) myositis; and the like.

Endocrine conditions: Diabetes (islet $\beta$-cells); hypothyroidism and hyperthyroidism (thyroid cells); hyperparathyroidism (parathyroid cells); polycystic ovaries (stromal cells of ovary); and the like.

Infectious diseases. Tuberculosis (monocytes/macrophages); bacterial infections (granulocytes); abscesses and other localized tissue infections (granulocytes); viral infections (lymphocytes); diabetes foot disease and gangrene (white cells); and the like.

Vascular disorders. Atherogenesis (smooth muscle proliferation in arterial wall); cardiomyopathies (cardiac myocyte proliferation); and the like.

Occupational diseases and exposures. Susceptibility to coal dust for black lung (fibroblast proliferative response); susceptibility to skin disorders related to sun or chemical exposures (skin cells); and the like.

The isotope label suitable for use in vivo is prepared in accordance with conventional methods in the art using a physiologically and clinically acceptable solution. Proper solution is dependent upon the route of administration chosen. Suitable routes of administration may, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer a label in a local rather than systemic manner, for example, via injection of the label directly into a specific tissue, often in a depot or sustained release formulation.

Determination of a detectable amount of the label is well within the capabilities of those skilled in the art.

6. EXAMPLE: MEASUREMENT OF CELL PROLIFERATION BY LABELING DNA WITH STABLE ISOTOPE-LABELED GLUCOSE 6.1. Materials and Methods 6.1.1. Isolation of Deoxyribonucleosides from DNA DNA was prepared from cells or tissues by phenol-chloroform-isoamyl alcohol extraction of cell suspensions or tissue homogenates. Yield and purity were confirmed by optical density. After heat denaturation, DNA was hydrolyzed enzymatically to deoxyribonucleosides by sequential digestion with nuclease P1, phosphodiesterase, and alkaline phosphatase, as described by Crain et al. (Crain, 1990, *Methods Enzymol.* 193:782–790). Nucleoside yield and purity were confirmed by HPLC using a C-18 column and water-methanol gradient (Shigenaga et al., 1994, *Methods Enzymol.* 234:16–33).

6.1.2. Derivatization of Deoxyribonucleosides and Analysis by GAS Chromatography Mass Spectrometry (GC-MS)

Figure 3:
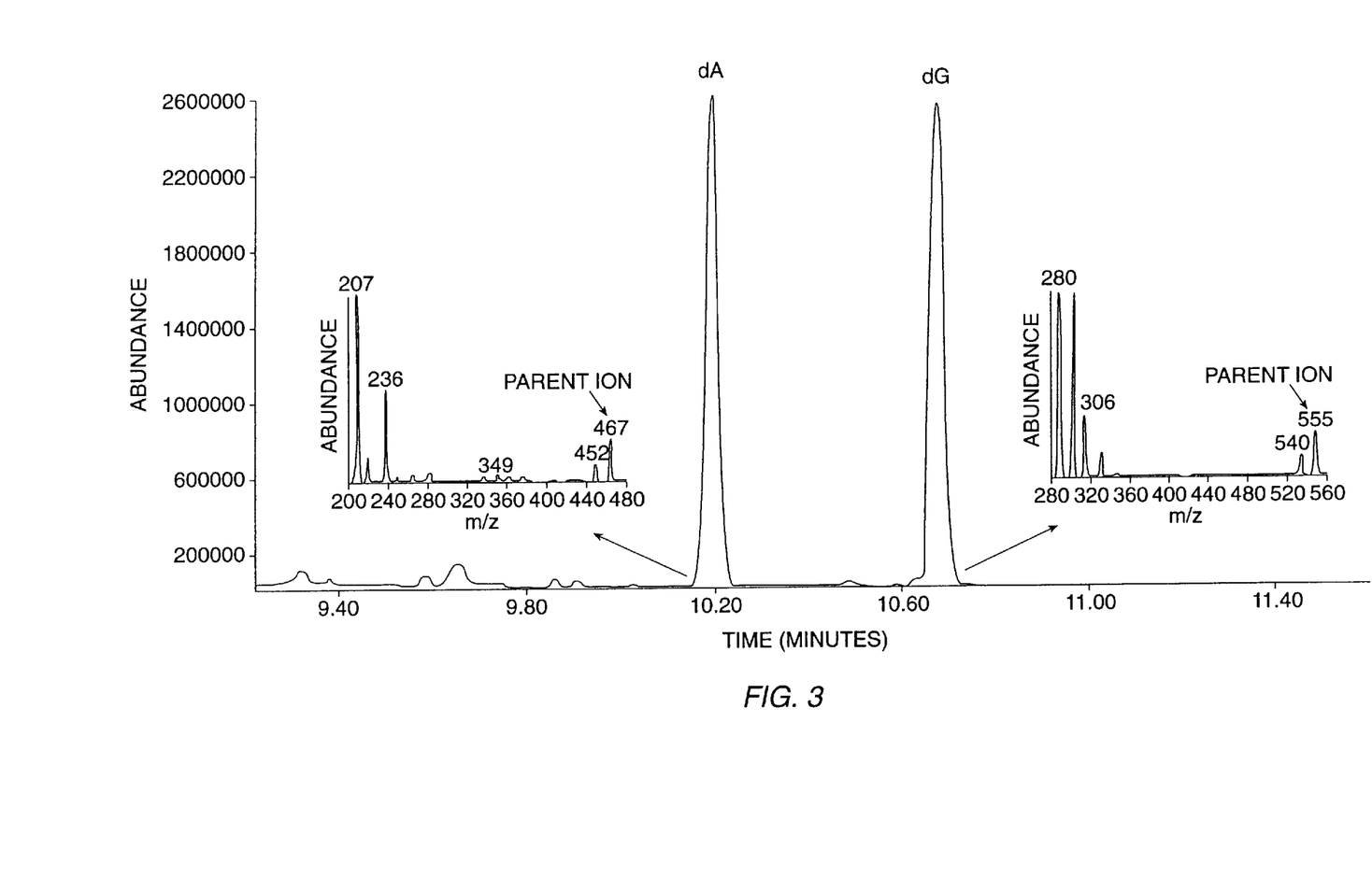
FIG. 3. GC-MS of DNA digest (total ion current). Mass spectra of dA and dG peaks are shown as insets.

Trimethylsilyl derivatives of nucleosides were synthesized by incubation of lyophilized hydrolysates with BSTFA: pyridine (4:1) at 100° C. for 1 hour. Samples were analyzed by GC-MS (DB-17 HT column, J&W Scientific, Folsom Calif.; HP 5890 GC and 5971MS, Hewlett Packard, Palo Alto, Calif.). Abundances of ions at mass to charge ratio (m/z) 467 and 469 were quantified under selected ion recording mode for deoxyadenosine (dA); and m/z 555 and 557 were monitored for deoxyguanosine (dG). Under the derivatization and GC-MS conditions employed, the purines (dA and dG) gave larger peaks (FIG. 3) than the pyrimidines, resulting in greater sensitivity and a higher signal to noise ratio. To measure the enrichment of glucose, plasma or culture media were deproteinized with perchloric acid and passed through anion and cation exchange columns (Neese et al., 1995, *J. Biol. Chem.* 270:14452–14463). The glucose penta-acetate derivative was formed by incubation with acetic anhydride in pyridine. GC-MS analysis was performed as described previously (Neese et al., 1995, *J. Biol. Chem* 270:14552–14663), monitoring m/z 331 and 333 under selected ion recording.

6.1.3. In Vitro Studies

Initial studies of label incorporation from $[6,6-^2H_2]$ glucose into cellular DNA were performed in tissue culture cell lines. Two cell lines were used: a hepatocyte cell line, HepG2, and a lymphocytic cell line, H9, which is a CD4$^+$ T cell line. HepG2 cells were grown in 10 ml dishes with alpha-modified Dulbecco's minimum essential media (MEM). H9 cells were grown in suspension in RPMI 1640. Both were grown in the presence of 10% dialyzed fetal calf serum and antibiotics (all reagents were obtained from Gibco-BRL, Gaithersburg, Md., except where stated). In both cases the number of cells present was measured by counting an aliquot on a Coulter ZMO901 cell counter. For HepG2 cells, plating efficiency was corrected for by counting an identical plate at the beginning of each labeling phase. Cells were labeled by addition of $[6,6-^2H_2]$ glucose (Cambridge Isotope Laboratories, Andover, Mass.) such that labeled glucose constituted 10–20% by weight of total glucose present (100 mg/L for MEM-a and 200 mg/L for RPMI 1640). In some experiments, glucose free medium was used and only 100% labeled glucose was present in the medium. Additional experiments were carried out in the presence of $[U-^{13}C_6]$ glucose and $[2-^{13}C_1]$ glycerol (Cambridge Isotope Laboratories, Andover, Mass.).

6.1.4. Animal Studies

Figure 2:
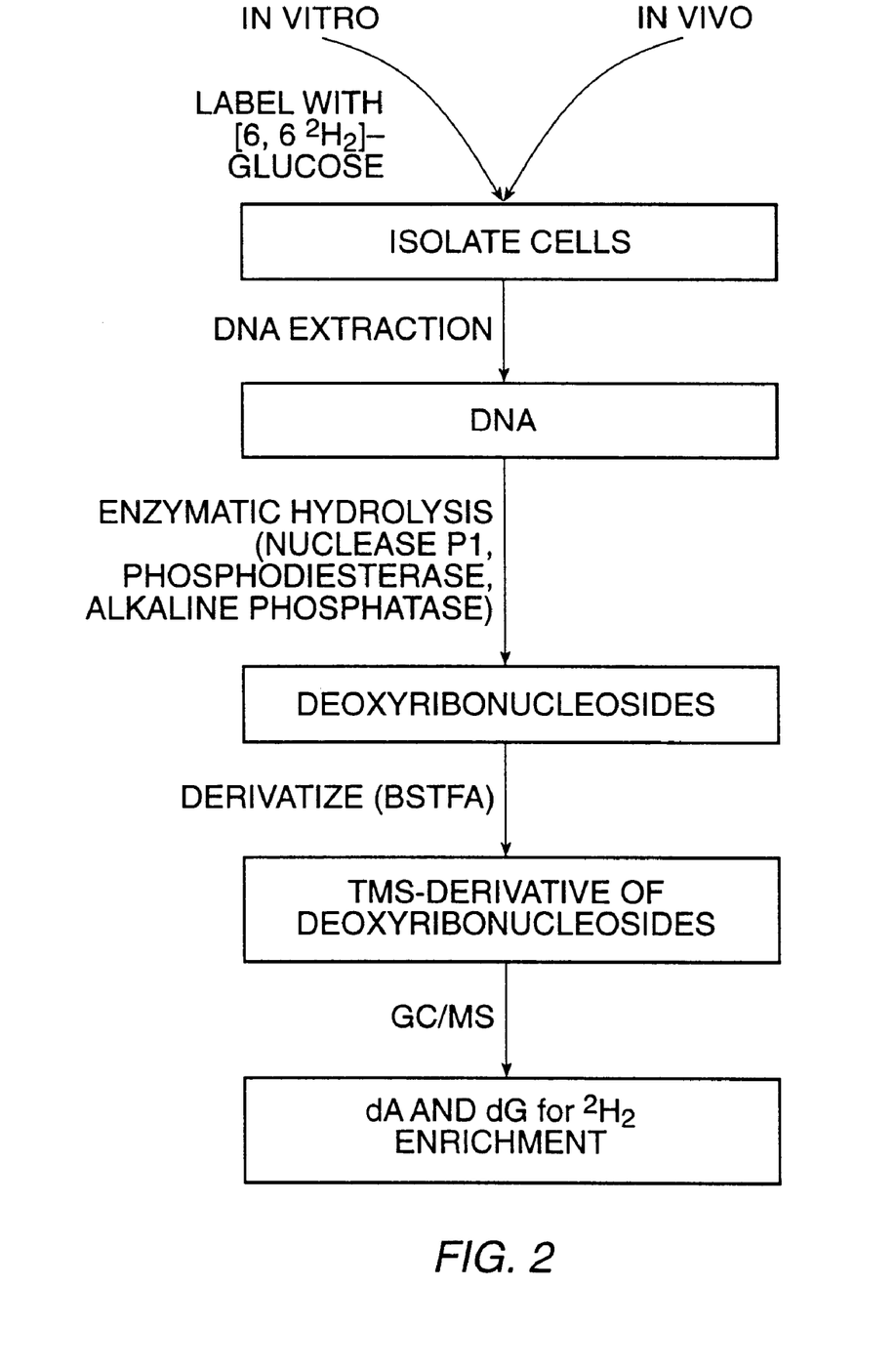
FIG. 2. Overview of a specifically exemplified method for measurement of DNA synthesis by incorporation of [6,6-$^2$H$_2$] glucose.

Four rats (approximately 250 g) were infused with labeled glucose. Intravenous canulae were placed under anesthesia (Hellerstein et al., 1986, *Proc. Natl. Acad. Sci. USA* 83:7044–7048). After a 24–48 hr recovery period, $[6,6-^2H_2]$ glucose was infused as a sterile 46 mg/ml solution at 0.5 ml/hr for approximately 24 hours. Food was withdrawn at the beginning of the isotope infusion. This dose was expected to achieve average plasma glucose enrichments of about 10%, based on previous studies in fasting rats (Neese et al., 1995, *J. Biol. Chem.* 270:14452–14463). At the end of the infusion period, animals were sacrificed. Blood for plasma glucose enrichment and tissues for DNA extraction were collected and frozen prior to analysis. A section of the intestine approximately 30 cm in length was excised from just below the duodenum in each rat. The intestinal segments were everted and washed. Epithelial cells were released from the submucosa by incubation with shaking in buffer containing 5 mM EDTA at 37° C. for 10 min, as described by Traber et al. (Traber et al., 1991, *Am. J. Physiol.* 260:G895–G903). DNA was extracted from cell preparations, then hydrolyzed to nucleosides and analyzed by GC-MS (FIG. 2).

6.1.5. Studies of Granulocyte Kinetics in Human Subjects

In order to investigate the application of the methods of the invention in clinical settings, four volunteers received intravenous infusion of [6,6-$^2$H$_2$] glucose (60 g over 48 h) in the General Clinical Research Center at San Francisco General Hospital. One subject was a healthy normal volunteer and the other three were HIV-seropositive men, who were participating in lymphocyte kinetic studies (blood CD4 cell counts in the range 215–377/mm$^3$). None had a clinically apparent infection at the time of the infusion. In order to enable high and relatively constant enrichments of plasma glucose and maximize labeling of cellular DNA, dietary carbohydrate was restricted (mean intake 46 g/d) during the 2-day period of the infusion. A heparinized blood sample was drawn at baseline and every 12 hr during the infusion, for estimation of plasma glucose enrichment. After the 48-hr infusion, blood was collected daily for 10 days and granulocytes and mononuclear cells were separated by gradient centrifugation (Vacutainer CPT, Becton Dickinson, Franklin Lakes, N.J.). Granulocyte DNA was extracted, hydrolyzed to nucleosides and analyzed by GC-MS, as described in Section 6.1.2, supra. All procedures received prior approval by the University of California at San Francisco Committee on Human Research and the University of California at Berkeley Committee for the Protection of Human Subjects, and written informed consent was obtained from subject for all procedures carried out.

6.2. Results

6.2.1. Development of Analytic Method

Derivatization is required to volatilize deoxyribonucleosides for GC-MS analysis (Blau and Halket, 1993, *Handbook of Derivatives for Chromatography* 2nd ed.). The highest abundances with TMS derivatization was observed, compared to methylation or acetylation. The GC-MS scans of a typical TMS-derivatized sample, analyzed under electron impact ionization, are shown (FIG. 3). dA and dG eluted from the GC column showed well defined peaks. As described previously (McCloskey, 1990, *Methods Enzymol.* 193:825–841), the dominant ions in the spectra were from the base moiety that were unlabeled from [6,6-$^2$H$_2$] glucose. The parent ions, m/z 467 and 557 for dA-TMS$_3$ and dG-TMS$_4$, respectively, were well represented and were present in a region of the mass spectrum with little background. Labeled samples contained an excess of the M+2 ions 469 and 557; the ratios of 469 to 467 and 557 to 559 were used for quantification.

Abundance sensitivity of isotope ratios (concentration dependance) was observed for dA and dG, as described for GC-MS (Neese et al., 1995, *J. Biol. Chem.* 270:14452–14463; Patterson and Wolfe, 1993, *Biol. Mass Spectrom* 22:481–486). Samples were therefore always analyzed at abundances matched to those in the standards used for baseline (natural abundance) subtraction, when calculating isotope enrichments. In enriched samples, the measured enrichments of dA were not significantly different from dG, as expected. Only data from dA are shown below.

6.2.2. In Vitro Cell Proliferation Studies

Figure 4A:
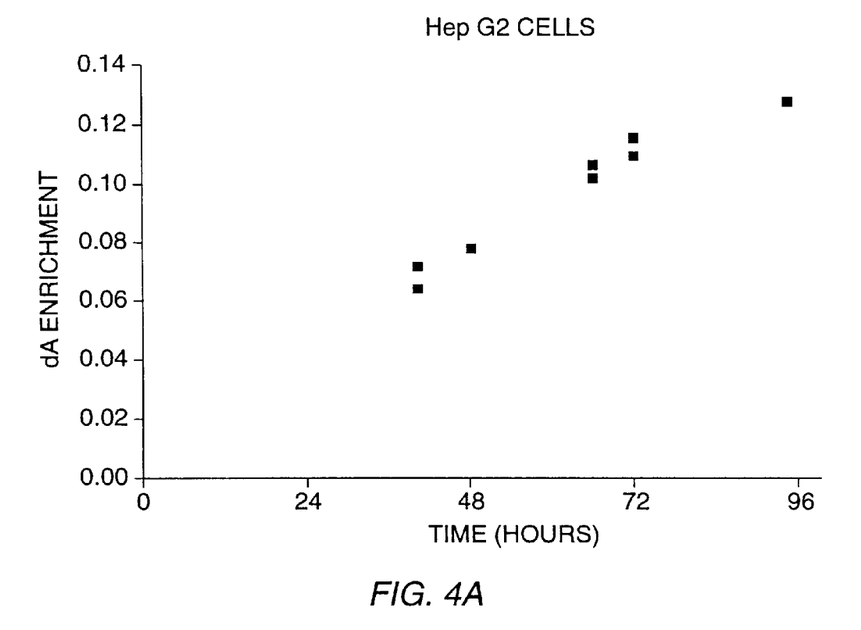
Figure 4B:
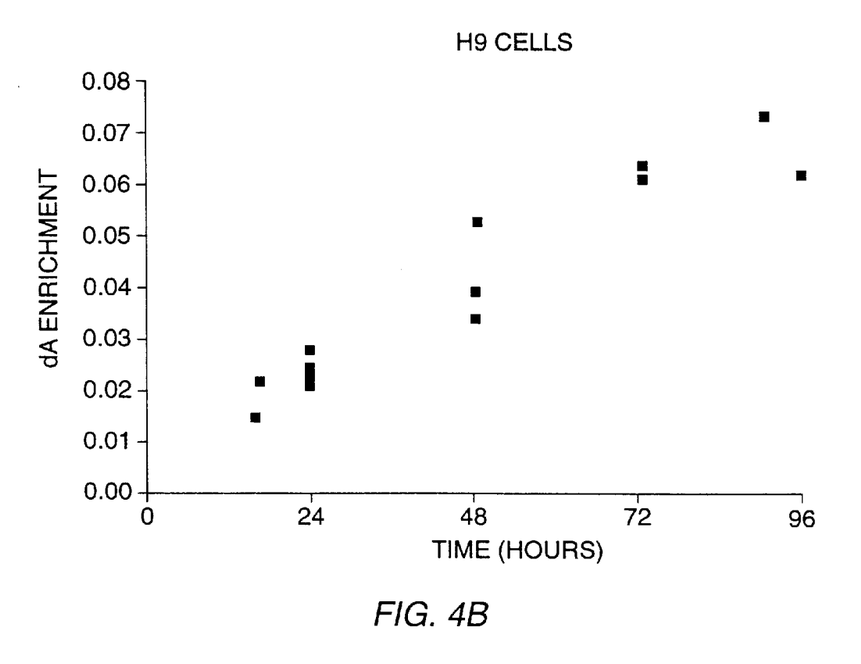
Figure 4C:
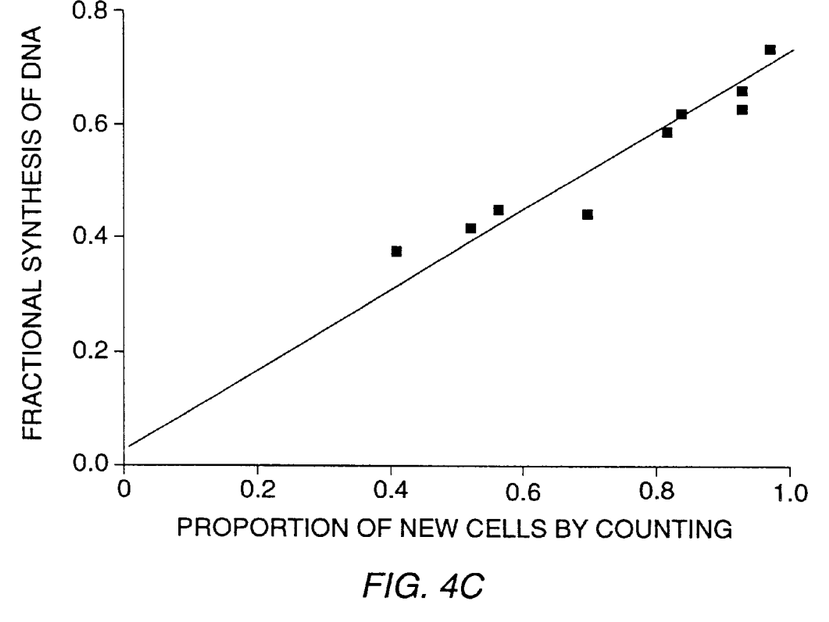
FIGS. 4C and 4D is a comparison of fractional synthesis of DNA by HepG2 cells (4C) and H9 cells (4D), calculated from $M_2$ enrichments of dA/medium glucose, with increase in cell numbers by counting.
Figure 4D:
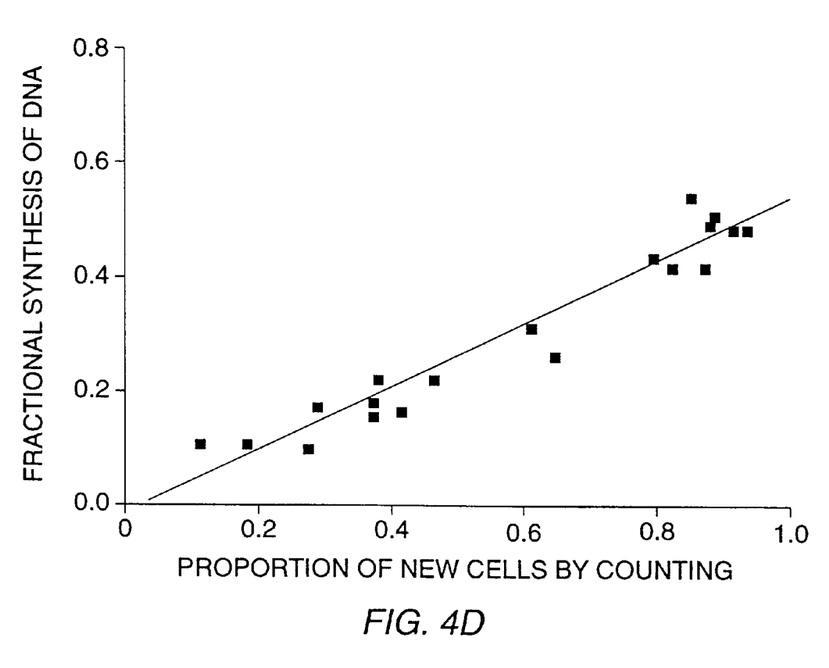

The enrichment of dA derived from cells grown in media containing 10–15% [6,6-$^2$H$_2$] glucose increased progressively with time (FIGS. 4A and 4B). This was demonstrated for both a hepatocyte cell line (HepG2) grown as monolayers on plates, and for a T-lymphocytic cell line (H9) grown in suspension. When compared to the number of cells measured by direct counting, dA enrichment correlated closely with the increase in cells by direct counting (FIGS. 4C and D). The correlation coefficient between the fraction of new DNA (calculated from the ratio of M2 enrichments in dA to medium glucose) and the percentage of new cells by direct counting was 0.984 with HepG2 cells and 0.972 for H9 cells.

The enrichment of the true intracellular dATP precursor pool for DNA synthesis using growing cells was equal in theory to the dA enrichment in DNA at 100% new cells (i.e., when only labeled DNA was present). Extrapolation of the labeling time course experiments to 100% new cells gave estimated plateau dA enrichments of 0.725 of the medium glucose enrichment for HepG2 cells and 0.525 for H9 cells (FIGS. 4A–D).

Figure 5A:
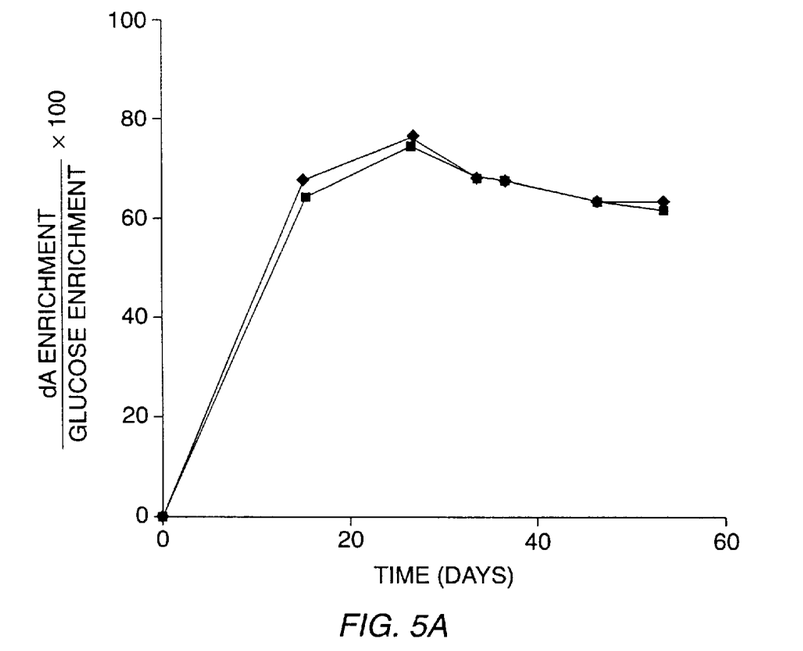
FIGS. 5A–5B. Enrichment of dA from DNA of (5A) hepatocyte (HepG2) and (5B) lymphocyte (H9) cell lines grown in media containing 100% [6,6-$^2$H$_2$] glucose for prolonged periods with repeated subcultures.
Figure 5B:
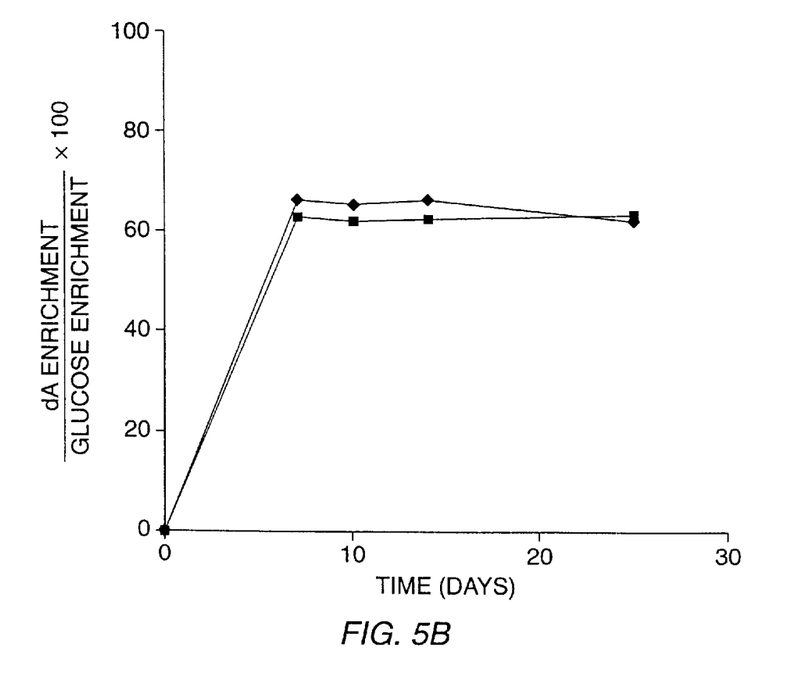

In order to test directly the relationship between enrichments of extracellular glucose and intracellular DNA precursors, cells were grown for prolonged periods in medium containing 100% [6,6-$^2$H$_2$] glucose with repeated replating or subculture of cells, for a total of 53 days for HepG2 cells and 25 days for H9 cells. At the end of the experiment, <0.1% of DNA present could be accounted for by the initial unlabeled cells. Maximum enrichment of dA was about 65% for both HepG2 and H9 cells (FIGS. 5A and B). One possible explanation for this dilution of extracellular labeled glucose could be the synthesis of glucose within the cell, e.g. from gluconeogenesis (GNG), since unlabeled amino acid precursors for GNG were present in the culture medium. Alternatively, some exchange of the label might have occurred during intracellular metabolism of glucose, either during glycolysis and passage through the tricarboxylic acid cycle or during the non-oxidative portion of the pentose-phosphate pathway (Wood et al., 1963, *Biochemische Zeitschrift* 338:809–847).

If intracellular unlabeled glucose from GNG were the dominant origin of dilution, dA from H9 cells might approach closer than the Hep G2 cells to 100% of medium glucose enrichment. However, this was not found to be the case (FIGS. 4A–D and 5A and B). A more direct test would be the incorporation of GNG precursors into dA in DNA by HepG2 cells. In order to test this hypothesis, both HepG2 and H9 were cultured in the presence of [2-$^{13}$C$_1$] glycerol. By applying the theory of combinatorial probabilities, or the mass isotopomer distribution analysis (MIDA) technique (Neese et al., 1995, *J. Biol. Chem.* 270:14452–14463; Hellerstein et al., 1992, *Am. J. Physiol.* 263:E988–E1001), the fraction of deoxyribose in dA that came from GNG could then be calculated. When HepG2 cells were grown in media to which [2-$^{13}$C$_1$] glycerol had been added at concentration of 20 µg/ml, negligible incorporation of $^{13}$C into dA was found. In the presence of 100 µg/ml [2-$^{13}$C$_1$] glycerol (approximately 2–3 times plasma glycerol concentrations), enrichment of both M$_{+1}$ and M$_{+2}$ ions was observed in dA. Applying MIDA revealed that 17.8% of dA pentose ring synthesis appeared to arise from GNG rather than utilization of extracellular glucose. H9 cells grown in the presence of 100 µg/ml [2-$^{13}$C$_1$] glycerol revealed no measurable GMG, as expected.

Duplicate pairs of cell cultures were also grown in the presence of 10% [6,6-$^2$H$_2$] glucose with and without the addition of unlabeled glycerol (100 µg/ml). Such unlabeled glycerol did not affect labeling in H9 cells; in HepG2 cells, incorporation into dA was reduced by 7%. Thus, it appears that the availability of GNG precursors had only a small effect on the labeling of DNA in cells capable of GNG and GNG does not fully explain the intracellular dilution of dA.

Figure 6A:
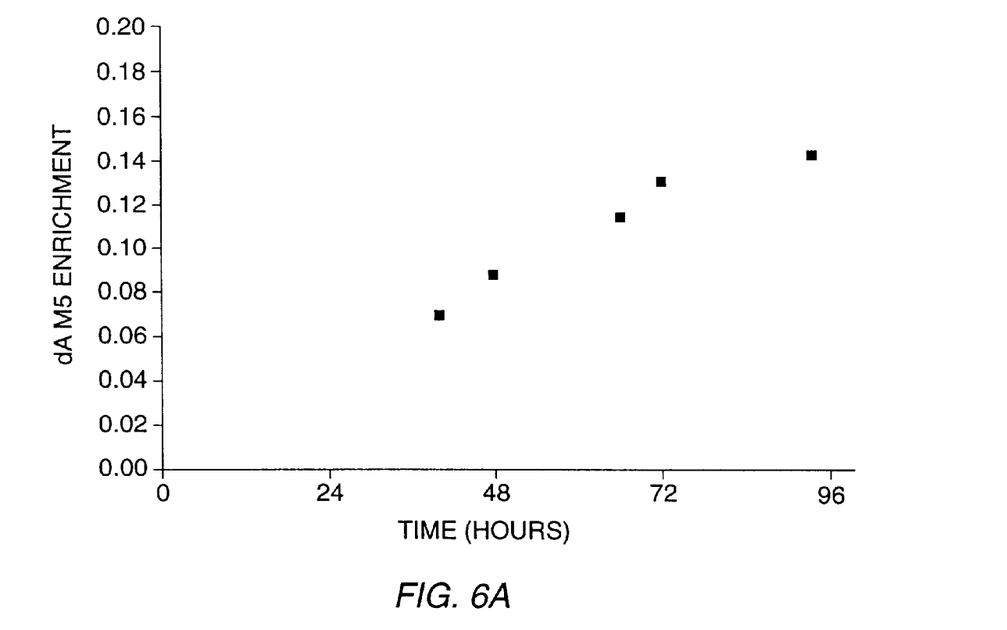
FIG. 6A demonstrates the enrichment of $M_5$ ion of deoxyadenosine from DNA of hepatocyte cell line (HepG2) cells grown in approximately 20% [U-$^{13}$C$_6$] glucose.
Figure 6B:
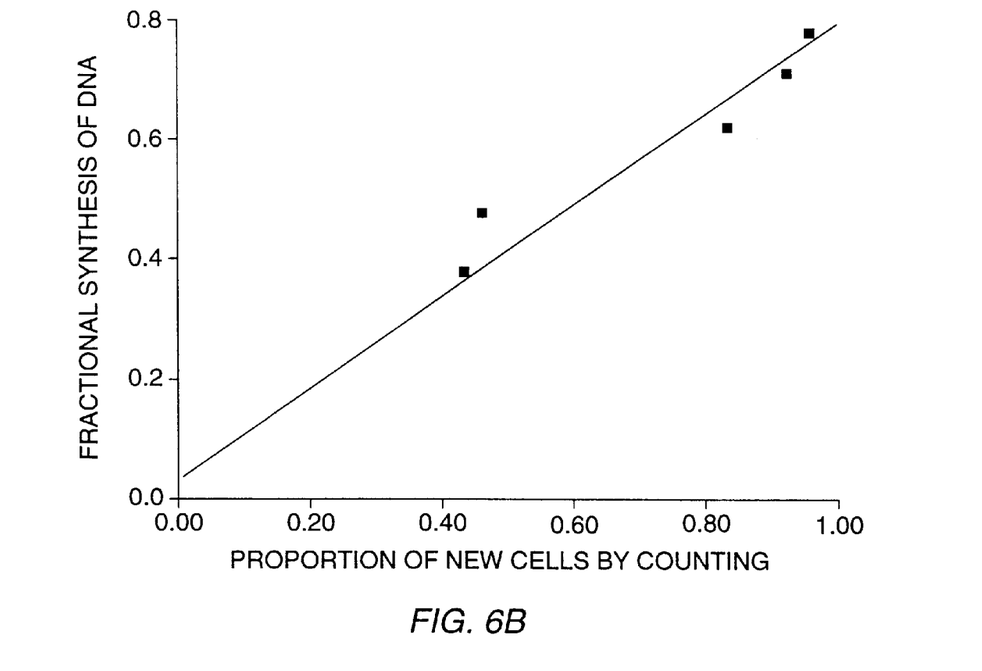
FIG. 6B is a comparison of fractional synthesis of DNA from $M_5$ labelling to proportion of new cells by direct counting.

If the roughly 35% dilution between extracellular glucose and dA in DNA were due to exchange of $^2$H for $^1$H in intracellular glucose cycles, carbon label in [U-$^{13}$C$_6$] glucose should undergo re-arrangement. Accordingly, HepG2 and H9 cells were grown in the presence of 10% [U-$^{13}$C$_6$]

glucose. If there were no metabolism through pathways such as the non-oxidative portion of the pentose phosphate pathway, the dNTP's from this precursor should retain all five labeled carbons and have a mass of $M_5$. The $M_5$ enrichment increased in a similar fashion to that observed with the $M_2$ ion from [6,6-$^2H_2$] glucose. An asymptote of approximately 80% of the extracellular enrichment was reached in HepG2 cells (FIGS. 6A and B) while in H9 cells the asymptote was approximately 60% of extracellular glucose enrichment. When the $M_0$ to $M_5$ spectrum was analyzed, enrichments of $M_2$, $M_3$, and $M_4$ ions were seen in addition to the expected enrichment of $M_5$. This phenomenon was observed in both H9 and HepG2 cells, although the relative abundance of these ions was greater from H9 cells.

The above cell culture experiments were performed in the absence of deoxyribonucleosides in the medium. Previous studies with lymphocyte cell lines (Reichard, 1978, *Fed. Proc.* 37:9–14; Reichard, 1988, *Ann. Rev. Biochem.* 57:349–374) have suggested that increasing the availability of extracellular deoxyribonucleosides does not reduce, and may even increase, activity of ribonucleoside reductase and the endogenous synthesis pathway for purine dNTP's (FIG. 1). To test directly the effects of increased availability of extracellular deoxyribonucleosides, HepG2 and H9 cells were grown in the presence of an equimolar mixture of the four deoxyribonucleosides. Two concentrations, 20 and 100 μM, were chosen to reproduce or exceed those prevailing in tissues; plasma concentrations are normally of the order of 1 μM and tissue concentrations may range between 1 and 100 μM (Cohen et al., 1983, *J. Biol. Chem.* 258:12334–12340). Six flasks of H9 cells were grown in parallel in media labeled with ca. 10% [6,6-$^2H_2$] glucose (Table 2).

TABLE 2

Effect of extracellular deoxyribonucleosides on incorporation of [6,6-$^2H_2$] glucose into dA in DNA

| | Extracellular Deoxyribonucleoside Concentration (μM) | | | | | |
|---|---|---|---|---|---|---|
| | 0 | 0 | 20 | 20 | 100 | 100 |
| Lymphocytes (H9) | | | | | | |
| dA/glucose ratio | 0.527 | 0.522 | 0.535 | 0.528 | 0.534 | 0.514 |
| Fraction new cells (by counting) | 0.849 | 0.851 | 0.867 | 0.856 | 0.839 | 0.822 |
| Extrapolated dA/glucose (100% new cells) | 0.620 | 0.613 | 0.617 | 0.617 | 0.637 | 0.626 |

TABLE 2-continued

Effect of extracellular deoxyribonucleosides on incorporation of [6,6-$^2H_2$] glucose into dA in DNA

| | Extracellular Deoxyribonucleoside Concentration (μM) | | | | | |
|---|---|---|---|---|---|---|
| | 0 | 0 | 20 | 20 | 100 | 100 |
| Hepatocytes (HepG2) | | | | | | |
| dA/glucose ratio | 0.386 | 0.385 | 0.381 | 0.370 | 0.339 | 0.344 |
| Fraction new cells (by counting) | 0.568 | 0.589 | 0.536 | 0.565 | 0.626 | 0.570 |
| Extrapolated dA/glucose (100% new cells) | 0.680 | 0.653 | 0.711 | 0.655 | 0.541 | 0.603 |

Two were grown without added deoxyribonucleosides, two were grown at the lower and two at the higher deoxyribonucleoside concentrations. After 90 hours, 85% of cells were new by counting. The experiment was also performed with HepG2 cells, yielding an average increase in cell number representing about 58% new cells. In H9 cells the presence of extracellular deoxyribonucleosides at either 20 or 100 μM did not reduce the incorporation of label from glucose into dA and thus did not appear to suppress the activity of the de novo nucleotide synthesis pathway. In HepG2 cells there was no appreciable reduction in incorporation at 20 μM, although there was a small (ca. 12%) reduction at 100 μM. In H9 cells, the extrapolated ratio of dA/glucose at 100% new cells (based on cell counting) was reproducibly between 62–64%. For HepG2 cells, the ratio ranged between 54–71%.

6.2.3. In Vivo Labeling of DNA: Animal Studies

In rats (n=4) receiving intravenous infusion of [6,6-$^2H_2$] glucose, plasma glucose enrichment at sacrifice was 13.2±0.9%. The mean plasma glucose enrichment for the whole 24 hour infusion period was less than this value because plasma glucose enrichment progressively increased during fasting, as the Ra glucose progressively fell (Rocha et al., 1990, *Eur. J. Immunol.* 20:1697–1708). The mean plasma glucose enrichment was estimated from two rats receiving labeled glucose infusion, and in which repeated blood samples were taken via arterial blood-drawing line. The mean enrichment for the 24h fasting period was 0.70 of the final enrichment; accordingly, this value was used for calculating the mean glucose enrichments for the four experimental rats (9.2±0.6%).

Differing enrichments were found in dA from the three tissues studied (Table 3).

TABLE 3

In vivo incorporation of [6,6-$^2H_2$] glucose into dA in DNA in various tissues in rats

| Tissue | dA Enrichment (%) | Percent New Cells | | Turnover time (d) | | Rate Constant, K (d$^{-1}$) | | $t_{1/2}$ (d) | |
|---|---|---|---|---|---|---|---|---|---|
| | | Uncorrected | Corrected | Uncorrected | Corrected | Uncorrected | Corrected | Uncorrected | Corrected |
| Intestinal epithelium | 3.18 ± 0.24 | 34.6 ± 4.2 | 53.2 ± 6.5 | 2.83 ± 0.37 | 1.84 ± 0.24 | — | — | — | — |
| Thymus | 2.33 ± 0.08 | 25.3 ± 2.2 | 38.9 ± 3.1 | — | — | 0.302 ± 0.030 | 0.51 ± 0.058 | 2.31 ± 0.23 | 1.36 ± 0.15 |
| Liver | 0.25 ± 0.06 | 2.7 ± 0.5 | 4.2 ± 0.9 | — | — | 0.028 ± 0.005 | 0.044 ± 0.008 | 25.4 ± 4.9 | 16.2 ± 3.1 |

Mean plasma glucose enrichment was 9.2 ± 0.6% and mean duration of infusion was 23.2 ± 0.1 hr.
Uncorrected calculations use plasma glucose enrichments as precursor for DNA synthesis; corrected calculations use a correction factor of 0.65 × plasma glucose enrichment to account for dilution in the intracellular precursor pool (see text).
A linear kinetic model was used for intestinal epithelium; an exponential model was used for thymus and liver.

For intestinal epithelial cells, a life-span (linear) kinetic model was employed based on the assumption that new cells divided, lived for a fixed period of time and then died in the order in which they were formed, representing the progression of intestinal epithelial cells from crypt to villus tip (Lipkin, 1987, *Physiol. Gastrointest. Tract*, pp. 255–284, Ed. Johnson, L. R.). A turnover time of 2.8±0.4d was calculated (uncorrected, using plasma glucose enrichments to represent intracellular dATP) or 1.8±0.2d (corrected, using plasma glucose with a 35% intracellular dilution factor). For thymus and liver a random replacement (exponential) model was applied. Thymus had a 10-times more rapid turnover than liver (Table 3).

6.2.4. Clinical Studies of Granuloctye Kinetics in Human Subjects

Figure 7:
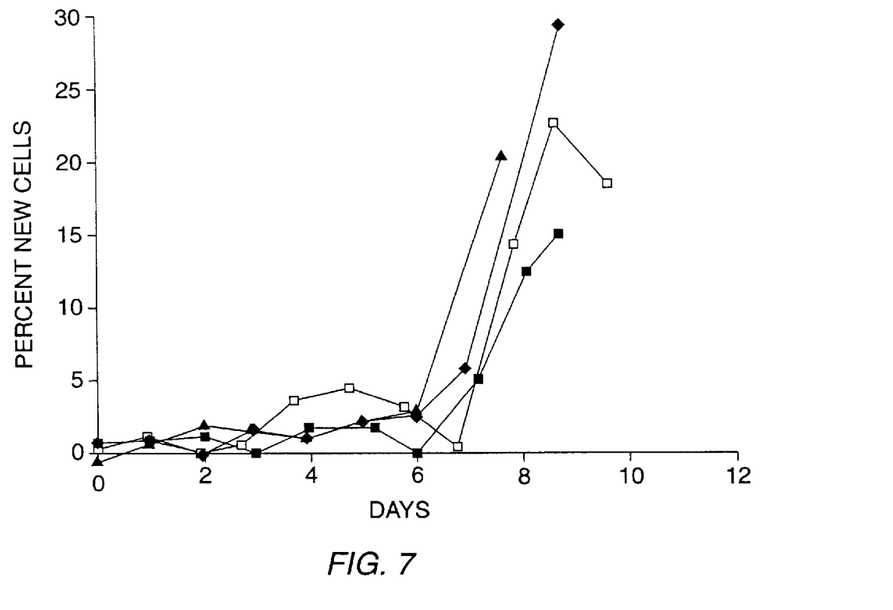
FIG. 7. Fractional synthesis of granulocytes in peripheral blood from 4 subjects following two-day infusion of [6,6-$^2$H$_2$] glucose, commencing at time zero. Open symbols, control subject; closed symbols, HIV-infected subjects. Fraction of new cells was calculated by comparison of dA enrichment to average plasma glucose enrichment, after correcting for estimated 35% intracellular dilution.

As part of a study of T lymphocyte kinetics in AIDS, three HIV seropositive men and one HIV seronegative man received an infusion of $[6,6-^2H_2]$ glucose (1.25 g/hr for 48 hr). All were clinically stable at the time of investigation. Absolute granulocyte counts were 1.5, 0.9, and $2.4\times10^9$/L, respectively, in the HIV-positive subjects and $2.4\times10^9$/L in the control subject. The infusions were well tolerated. Mean plasma glucose enrichments of 15.3±2.4 molar percent excess were achieved (rate of appearance of glucose about 2 mg/kg/min). Granulocytes were isolated and dA enrichment measured from DNA. For the first 6 days following the infusion, very low proportions of labeled cells were seen in the circulation (FIG. 7), followed by the appearance of labeled cells starting on days 6–8. Enrichments at day 8 indicated about 25% new cells present (corrected).

6.2.5. Measurement of T Cell Proliferation in HIV Infection

T cell proliferation rates in individuals infected with human immunodeficiency virus (HIV) was measured by the methods of the invention. An intravenous infusion of $[6,6-^2H_2]$ glucose was performed in men with well-maintained CD4$^+$ T cell numbers (>500/mm$^3$) or low CD4$^+$ counts (<200/mm$^3$). The infusion was for 48 hr at 1.25 g $[6,6-^2H_2]$ glucose/hr, to achieve 10–15% proportion of labeled glucose molecules in the blood plasma (10–15% enrichment). Blood (20–30 cc) was collected daily during the infusion and for the following 10 days.

Figure 8:
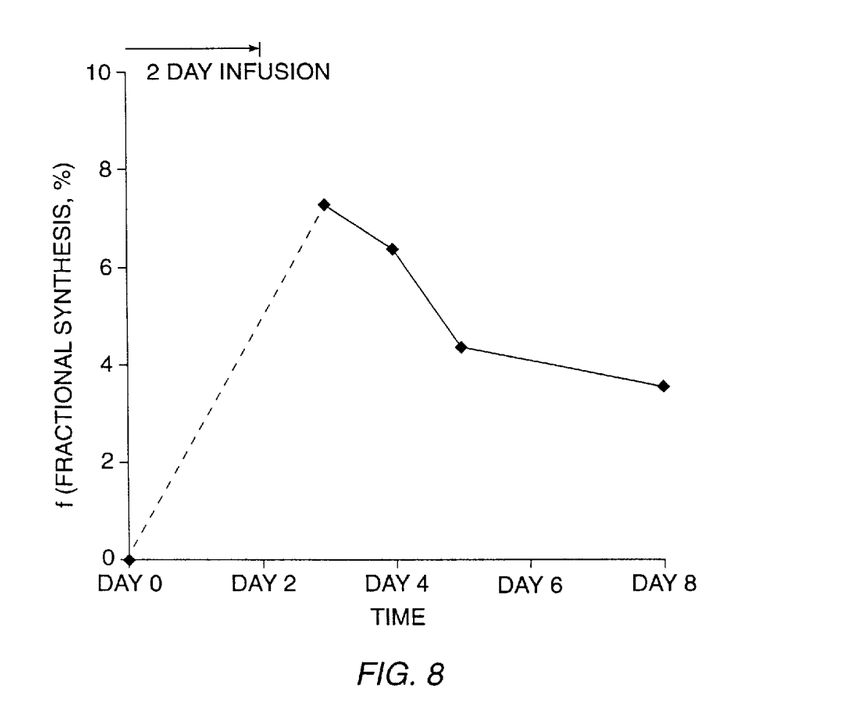
FIG. 8. Fractional synthesis of CD4$^+$ lymphocytes obtained from peripheral blood of an HIV infected patient following two-day infusion of [6,6-$^2$H$_2$] glucose.

Mononuclear cells were isolated using PT® tubes; and CD4$^+$ cells were then isolated using either magnetic bead immunoseparation (Dynabeads®) or fluorescent activated cell sorting to isolate $10^6$ cells. DNA from isolated cells was recovered using a commercial kit (Quiagen®). DNA was hydrolyzed to free deoxyribonucleosides enzymatically with nuclease P$_1$, phosphodiesterase, and alkaline phosphatase; the hydrolysate was derivatized with FSTFA to the trimethylsilyl derivatives of deoxyribonucleosides, which were injected into a table top GC-MS instrument. The dA and dG peaks from the GC effluent were monitored by selected ion recording mass spectrometry and m/z 467 and 469 (for dA) and m/z 555 and 557 (for dG) were quantified, through comparison to standard curves of commercially labeled material analyzed concurrently (e.g., $[5,5-^2H_2]$ dA purchased from CIL, Cambridge, Mass.). Standard curves were abundance matched between standards and sendes to correct for concentration sensitivity of isotope ratios. Enrichments in dA and dG from CD4$^+$ and CD8$^+$ T cells were in the rate 0.00 to 1.50 percent labeled species. By comparison to the plasma glucose isotope enrichment (10–15 percent labeled species) with a 35% dilution correction and application of the precursor-product relationship (Hellerstein and Neese, *American Journal of Physiology* 263:E988–1001, 1992), the preparation of newly synthesized DNA strands was quantified. Peak values were at 2–3 days after the start of $[6,6-^2H_2]$ glucose infusions and reached 15–20% newly synthesized DNA strands, and thus 15–20% newly proliferating cells (FIG. 8). The die away curves of dA or dG labeling between days 4 and 10 revealed the destruction rate of the label and therefore recently dividing population of cells (Hellerstein and Neese, 1992, *American Journal of Physiology* 263: E988–1001). Destruction rates of labeled cells was generally higher than for the general population of cells implying selective death of recently divided and activated cells. The effect of CD4$^+$ T cell proliferation and destruction of anti-retroviral therapies was then determined, by repeating the $[6,6-^2H_2]$ glucose infusion after 8–12 weeks of therapy.

In conclusion, a method for measuring DNA synthesis using stable isotope labels and mass spectrometry was developed for measuring cell proliferation. This method involves no radioactivity and potential toxic metabolites, and is thus suitable for use in humans.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for measuring cellular proliferation, comprising contacting a cell with a detectable amount of a stable isotope label which is incorporated into DNA via de novo nucleotide synthesis pathway, detecting the label in the DNA, and determining an amount of label incorporated in the DNA to measure cellular proliferation.

2. The method of claim 1 in which the label is incorporated into deoxyribose.

3. The method of claim 2 in which the label is a labeled glucose.

4. The method of claim 3 in which the DNA is hydrolyzed to deoxyribonucleosides.

5. The method of claim 4 in which the label is detected by mass spectrometry.

6. The method of claim 1 in which the label is incorporated into a purine.

7. The method of claim 1 in which the label is incorporated into a pyrimidine.

8. A method for measuring cellular proliferation in a subject, comprising administering a detectable amount of a stable isotope label into the subject, which label is incorporated into DNA via de novo nucleotide synthesis pathway, detecting the label in the DNA, and determining an amount of label incorporated in the DNA to measure cellular proliferation.

9. The method of claim 8 in which the label is incorporated into deoxyribose.

10. The method of claim 9 in which the label is a labeled glucose.

11. The method of claim 10 in which the DNA is hydrolyzed to deoxyribonucleosides.

12. The method of claim 11 in which the label is detected by mass spectrometry.

13. The method of claim 8 in which the subject is a human.

14. The method of claim 8 in which DNA is extracted from cancer cells.

15. The method of claim 8 in which DNA is extracted from lymphocytes.

16. The method of claim 15 in which DNA is extracted from CD4$^+$ cells.

* * * * *